United States Patent [19]

Carter

[11] 4,242,531
[45] Dec. 30, 1980

[54] OLEFIN DIMERIZATION

[75] Inventor: Cecil O. Carter, Bartlesville, Okla.

[73] Assignee: Phillips Petroleum Company, Bartlesville, Okla.

[21] Appl. No.: 933,345

[22] Filed: Aug. 14, 1978

[51] Int. Cl.$^3$ .......................... C07C 3/10; C07C 3/18; C07C 3/21

[52] U.S. Cl. .................................. 585/512; 585/510; 585/523

[58] Field of Search ............ 260/683.15 R, 683.15 D; 585/512, 510, 523

[56] References Cited

U.S. PATENT DOCUMENTS

| | | | |
|---|---|---|---|
| 2,360,632 | 10/1944 | Mann et al. | 260/683.15 R |
| 2,846,427 | 8/1958 | Findlay | 260/683.15 R |
| 3,126,365 | 3/1964 | Hooker | 260/949 |
| 3,257,363 | 6/1966 | Miller et al. | 260/88.2 |
| 3,437,705 | 4/1969 | Jones | 260/683.15 R |
| 3,437,707 | 4/1969 | Sulzbach | 260/683.15 R |
| 3,499,826 | 3/1970 | Sulzbach | 260/683.15 R |
| 3,631,121 | 12/1971 | Hutson | 260/683.15 D |

*Primary Examiner*—Arthur P. Demers

[57] ABSTRACT

Olefins are dimerized in a loop reactor with flashing of the reactor effluent in a flashing zone within the loop. A subsequent flash in a second flashing zone can also be used for the removal of product as flash vapor. In another embodiment, separated product dimers or product heavies are used as absorbents for unreacted ethylene. The use of a vapor-liquid contacting device incorporated in the loop reactor is especially helpful in the dimerization of an olefin when the olefin is available in low-concentration gas streams. A thermosiphon loop reactor can also be used for low-concentration olefin streams to minimize the power requirements as the energy of the feed gas is used to induce the reactor circulation.

17 Claims, 4 Drawing Figures

OLEFIN DIMERIZATION

BACKGROUND OF THE INVENTION

This invention relates to the dimerization of olefins in a loop reactor. In another aspect, this invention relates to the dimerization of olefins in a loop reactor that has a flash zone located within the loop thereby allowing the product to be removed as a vapor from the flash. In another aspect, this invention relates to the dimerization of olefins wherein two flashing zones are used to remove the product as a vapor. In still another aspect, this invention relates to the concentration of a nonvolatile homogeneous catalyst for subsequent recycling of catalyst to the reactor loop by flashing off product. In yet another aspect, this invention relates to a dimerization process of olefins wherein product heavies are used as an absorbent in an absorber. In still another aspect, the invention is concerned with the use of product heavies to absorb unreacted olefin and recycle the olefin to the loop reactor in a dimerization process. In still another aspect, this invention relates to a dimerization process in which dimer product is utilized as an absorbent for unreacted ethylene. The invention also relates to a dimerization process for olefins in a loop reactor in which a vapor-liquid contact device is contained within the loop and dimer product is used as an absorbent for unreacted ethylene within the device. The invention is also concerned with the use of the vapor-liquid contacting device contained within the loop of a loop reactor for low-concentration olefin feeds. In still another aspect, this invention relates to a dimerization process for olefins in a thermosiphon loop reactor using the energy of the feed gas to induce reactor circulation. This invention also relates to the use of a thermosiphon loop reactor in order to dimerize olefins in a low-concentration feed.

Another aspect of this invention relates to the apparatus used to dimerize olefins. In one aspect, the invention relates to olefin dimerization apparatus comprising a flashing means in the continuous loop of a loop reactor. In another aspect, this invention relates to olefin dimerization apparatus comprising two flashing means. In another aspect, this invention relates to olefin dimerization apparatus comprising a vapor-liquid contactor in the continuous loop of a loop reactor. In still another aspect, this invention relates to olefin dimerization apparatus comprising a thermosiphon loop reactor.

The dimerization of olefins is a well-known process in the art, e.g., U.S. Pat. No. 3,631,121 and U.S. Pat. No. 3,485,881. Olefin dimerization processes are applicable to olefins in general, however, dimerization is an especially attractive method for producing butylenes from ethylene for subsequent use in alkylation, dehydrogenation to butadiene and other chemical processes. Problems arise in dimerization processes, however, in that the process suffers from low selectivity to the dimer with much of the feed being converted to trimers and product heavies. It is known that selectivity can be improved by using shorter reactor residence time, but the disadvantages of this approach are low ethylene conversion and low catalyst productivity.

Other problems arise when the feed stream is low in olefin concentration, e.g. only a small amount of ethylene with the remainder of the feed stream being gases such as hydrogen, methane, ethane, etc. It would be desirable to remove the ethylene from the gas before the gas ends up as a fuel gas stream. The amount of olefin, e.g., ethylene, is so small, however, that it would be economically undesirable to use conventional equipment with the expensive power requirements of circulating the reaction medium through the loop reactor as well as costly recompression and the expense of a low temperature olefin recovery column.

Accordingly, it is an object of this invention to provide an improved and more economical process for olefin dimerization.

Another object of this invention is to provide an olefin dimerization process with improved olefin selectivity and conversion as well as catalyst productivity.

Another object of this invention is to provide an olefin dimerization process which recycles the olefin reactant yet avoids costly recompression and an expensive low temperature recovery column.

Another object is to provide a method for dimerizing an olefin from a low concentration stream to thereby obviate the need for olefin purification facilities.

Still another object of the invention is to minimize the power requirements of an olefin dimerization process using a loop reactor.

Other aspects, objects and advantages are apparent from a study of this disclosure, the drawings and the appended claims.

SUMMARY OF THE INVENTION

A process system has been devised which overcomes the deficiencies of prior art olefin dimerization processes such as low olefin conversion and low catalyst productivity as well as low selectivity of the olefin to the dimer. The present invention is also concerned with variations in the process system to enable one to minimize the power requirements of an olefin dimerization reaction. Embodiments of the invention have special application for the dimerization of low-olefin-concentration streams. This is especially true for a gas stream containing a low concentration, 20% by volume or less, of an olefin such as ethylene where an ethylene plant as such is not available. It is desirable to separate the olefin but not at the expense of building or using expensive olefin purification facilities. The dimerization processes of the invention can, therefore, be used to dimerize the olefin for easier separation without the expense of complex olefin purification facilities. The process is suitable for use with any dimerization catalyst.

In a first embodiment, most of the major product is removed as a vapor by flashing the reactor effluent in a flashing zone. The flashing zone is within the loop of the loop reactor and can, e.g., be the shell side of a heat exchanger. By removing most of the major product as a vapor from the flash, the catalyst can be retained in the reactor for a longer period of time, which thereby improves catalyst productivity.

In another embodiment, the reactor effluent is flashed in two stages thereby vaporizing most of the product and concentrating a catalyst in a small stream of heavies for recycle to the reactor. Unconverted olefin is recovered in an absorber utilizing a heavies product stream, which is a product of the process, as the absorbent. The absorbed olefin can thereby be recycled to the reactor in the liquid phase, avoiding costly recompression and the expense of a low temperature olefin recovery column.

The invention also contemplates the use of a liquid gas absorber contactor within the loop reactor in order to concentrate the olefin and thereby obviate the need for olefin purification facilities. Product dimer can be used as the absorbent and can be recycled from the product stripper for such use. This embodiment is especially useful for low olefin concentration streams, e.g., ethylene in a fuel gas stream.

In another embodiment, a thermosiphon type loop reactor is utilized to minimize the power requirements of the loop reactor in that the energy of the feed gas is used to induce reactor circulation. This embodiment is especially applicable for low-concentration olefin streams, e.g., about 20% by volume or less, wherein the dimer is more easily removed from the gas stream than the original olefin.

DETAILED DESCRIPTION OF THE INVENTION

This invention relates to the dimerization of olefins. The dimerization can take place in a loop reactor, a type of reactor which is well known in the art. The process and apparatus of the invention are suitable for use with any appropriate dimerization catalyst. The catalysts preferably employed, however, are those of any hydrocarbon-soluble nickel compound, alkyl aluminum halide, or mixture thereof, e.g., tri-n-butylphosphine nickel dichloride mixed with ethyl aluminum dichloride or bis(tri-n-butyl-phosphine)dichloronickel.

When the catalyst employed is a mixture of a hydrocarbon-soluble nickel compound and an alkyl aluminum halide, it is preferred that low aluminum/nickel molar ratios, e.g., molar ratios in the range of about 2.1 to about 7, are used in the catalyst components in order to minimize fouling. Further, with the use of low aluminum/nickel ratio catalysts the deposits that do form in the reactor and heat exchangers can be readily removed by washing with a 10 weight percent acetic acid solution.

Another factor in minimizing fouling of the apparatus is the material flow fluid velocity in the continuous, closed reaction zone. The maintenance of high fluid velocities, e.g., 6-20 feet/second, in the circulating reaction loop helps to minimize the formation of deposits. It is preferred to maintain a velocity of about 12 feet/second or higher for greatest success at minimizing fouling.

Suitable process conditions of temperature and pressure can vary greatly for this invention and can be easily determined by one skilled in the art.

The process is applicable to the dimerization of any suitable olefin, with the invention especially applicable to the selective dimerization of $C_2$ to $C_{10}$ olefins. Ethylene is the preferred olefin reactant, however, as ethylene dimerization is an attractive method for producing butylenes from ethylene for subsequent use in alkylation, dehydrogenation to butadiene and other chemical processes.

A better understanding of the invention will be obtained upon reference to the drawings. Although the drawings are discussed with reference to ethylene as the olefin reactant to be dimerized, it is emphasized that this should not limit the invention in any way. The invention is applicable to any olefin that can be dimerized but the discussion is limited to ethylene as that is the preferred olefin reactant.

Figure 1:
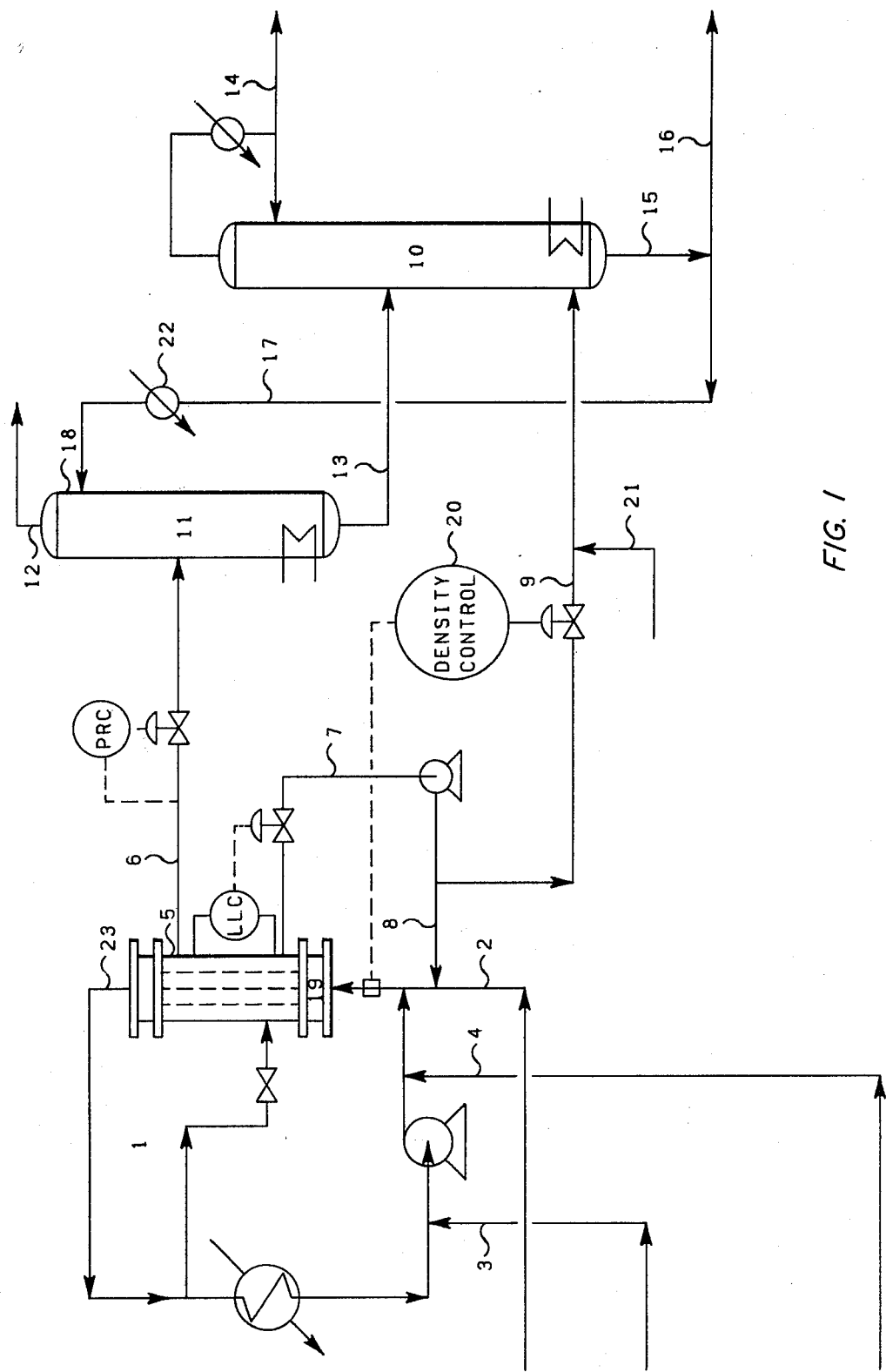
FIG. 1 is a schematic of the apparatus used in the olefin dimerization process wherein the product is removed from the loop reactor in a flashing zone.

FIG. 1 depicts an embodiment of the invention wherein ethylene is dimerized in a loop reactor and reactor effluent is flashed in a flashing zone located within the loop, thereby removing part of the excess thermal heat of the reaction and allowing part of the product dimer to be removed as flash vapor. The olefin reactant, e.g., ethylene, is introduced into a continuous closed path reaction zone 1, e.g., a loop reactor, via conduit 2. Catalysts selective to dimerization are added via 3 and 4, or, if only one catalyst were to be used, the catalyst can be added via either 3 or 4. The olefin reactant, ethylene, is thereby reacted in the presence of said catalyst selective to dimerization under such conditions as to result in the dimerization of the olefin. The reactor effluent is then flashed in a flashing zone 5 located within the continuous closed path reaction zone 1. Product dimer is removed via 6 from the flashing zone as flashed vapor. As an option, one can place a disengaging tank in line 6 thereby assuring that any entrained liquid would be separated from product vapor and returned to the flashing zone. The flashed vapor is passed through various separation units to yield a purified dimer product.

A portion of the flashed liquid from flashing zone 5 is recycled to the reaction zone via conduits 7 and 8. The remainder of the flashed liquid is passed to a recovery system, e.g. fractionator 10, for recovery of product dimer via conduits 7 and 9.

The material flow or process velocity of the continuous closed path recovery zone can vary, however, it is preferred to maintain the material flow at about 12 feet per second or higher as opposed to the more conventional flow of 6-8 feet per second. Maintaining the material velocity at such a rate can increase or extend the interval between cleaning the system from about 400 to about 4,000 hours, or ten times as long.

The flashed vapor from flashing zone 5 can be passed via 6 to an absorption zone 11 in order to recover the product dimer, as well as any product heavies, i.e., trimers, etc., from unconverted ethylene or other gases contained in the flashed vapor. The unconverted ethylene is removed via 12 and the product dimer and heavies are passed via 13 to fractionator 10. At fractionator 10, the product dimer, butene, is separated from the product heavies and recovered via line 14. The bottoms of the fractionator are composed of product heavies which are removed via 15 and passed to disposal or storage via 16 or recycled to absorber 11 via conduit 17 and cooler 22. The heavies are introduced into absorber 11 near the top 18 and act as an absorbent for the product dimer.

The flashing zone 5 can be a heat exchanger located within the loop reactor with the reactor effluent flashing in the shell side 19 of said heat exchanger. The heat exchanger, therefore, serves the dual purpose of cooling the solvent and reaction effluent, as well as removing most of the major product, butenes, as a vapor by flashing. By removing most of the butenes as a vapor from a flash, the catalyst can be retained in the reactor for a longer period of time and thereby improve catalyst productivity. The removal by flashing also eliminates a catalyst killing and removal step which would normally accompany a separation wherein the entire reactor effluent was passed to the separation facilities. As mentioned above, one can optionally place a disengaging tank in line 6. The disengaging tank assures that any entrained liquid would be separated from product vapor and thereby be returned to the heat exchanger.

The vaporization of most of the product by flashing concentrates the catalyst in a small stream of heavies for recycle to the reactor via conduits 7 and 8. A buildup of heavies in the system is controlled by directing a portion of the recycled flash liquid to the product fractionator via conduits 7 and 9. As indicated in FIG. 1, the flow of this stream to the product fractionator can be controlled by a density controller 20, or any other suitable analyzer means, on the recirculating reactor loop stream. It is also desirable to kill the catalyst in this stream passing to product fractionation in order to prevent the production of undesirable heavies in that column. This is done by the introduction of a small amount of water or steam 21 into the feed to the product fractionator.

By controlling process variables, i.e., reactor temperature, residence time, etc., ethylene conversion can be maintained at 99 percent, eliminating the need for ethylene recycle.

Figure 2:
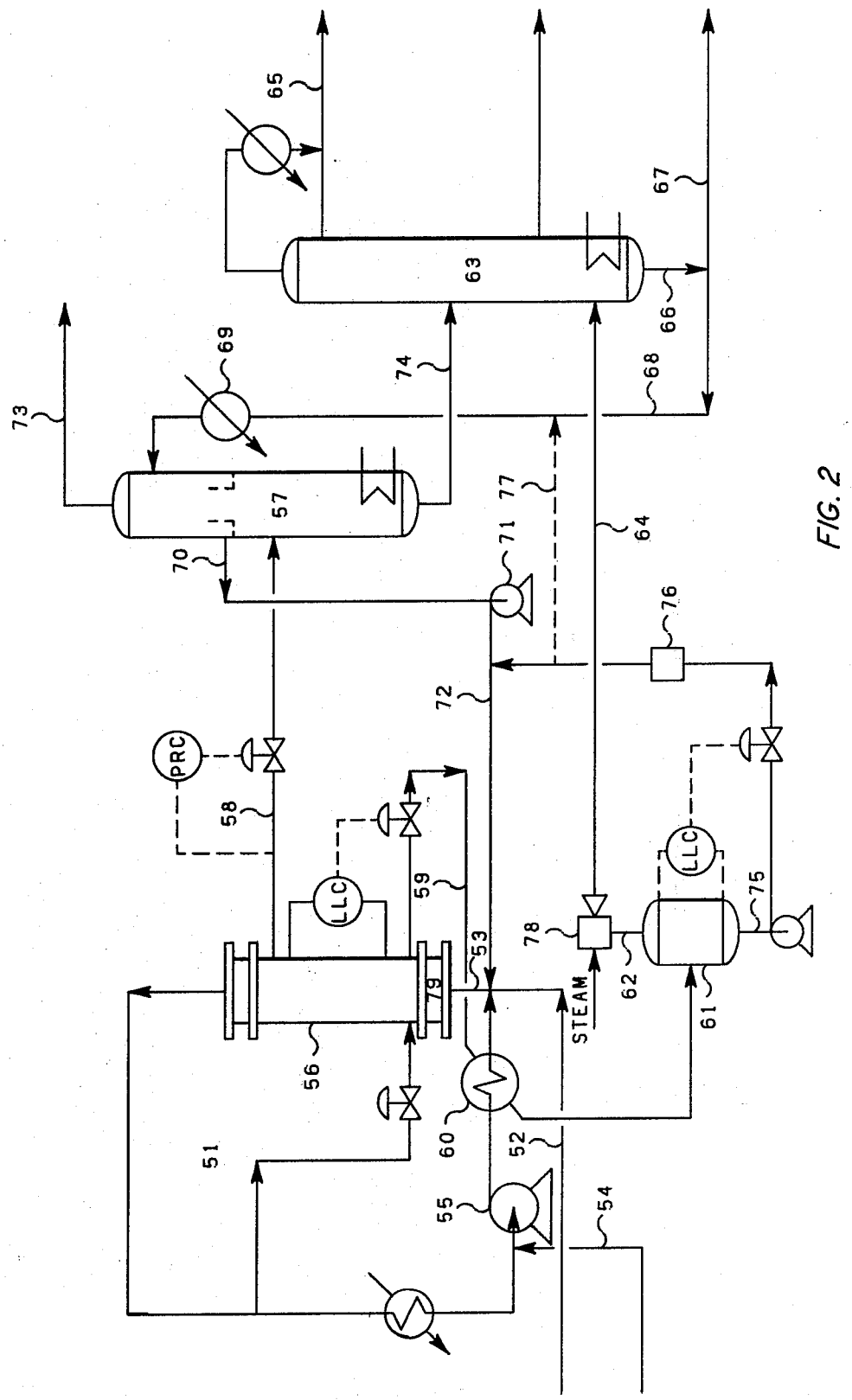
FIG. 2 is a schematic showing an olefin dimerization process wherein the reactor effluent is flashed in two stages. The drawing also shows the recycle of unreacted olefin absorbed in product heavies.

FIG. 2 depicts an embodiment of the invention wherein the reactor effluent is flashed in two stages. Gaseous ethylene or other selected olefin feed from line 52 enters the continuous closed path reaction zone 51 at 53. In order to initiate the dimerization reaction, suitable amounts of one, two, or more suitable catalysts are injected into the loop reactor system via 54. Examples of suitable catalysts are a mixture of ethyl aluminum dichloride and tri-n-butylphosphine nickel dichloride or just bis(tri-n-butylphosphine)dichloronickel. The conditions in the loop reactor are such as to promote the dimerization of the olefin, ethylene, in the presence of the catalyst. Circulation through the continuous closed path reaction zone is maintained by means of pump 55.

The reactor effluent is then flashed in flashing zone 56 which is located within the continuous closed path reaction zone. Overhead from this first flash zone passes to a deethanizer 57 via conduit 58. The resultant or residue liquid from the first flashing zone is passed via conduit means 59 through heat exchanger 60 to a second flashing zone 61. This second stage flash is at a lower pressure than the first stage and thereby removes product dimers, e.g., $C_4$ hydrocarbons, as well as product heavies, e.g., $C_8$, etc. The overhead from the second flash is removed via 62 and passed to fractionator 63 via conduit means 64. Fractionator 63 divides or separates the product stream into its various components, including the product dimer butenes which are removed overhead at 65. Bottoms of the fractionator 66, which comprises octenes and other product heavies are passed to disposal or storage via 67 with a portion recycled via 68 and heat exchanger 69 to the top of the deethanizer 57. The heavies stream is used as an absorbent for the unconverted ethylene. An ethylene-rich side stream is taken from the absorber at 70 and pumped by means of pump 71 back to the reactor via conduit 72. The use of the absorption section on a low-pressure column to recover the unreacted ethylene using a product heavies fraction as the solvent permits the operation of the fractionator train at a low pressure on flashed reactor effluent thereby allowing the absorbed ethylene to be recycled to the reactor in a liquid phase and avoiding costly recompression and the expense of a low-temperature ethylene recovery column.

Overhead inert gases from the deethanizer are removed via 73 and passed on for use as fuel gas. Bottoms from the deethanizer are passed via 74 to fractionator 63.

The bottoms of the second flash zone 61, which contain primarily spent catalyst, are removed via 75 and pumped back to the reactor. The spent catalyst, which has in the prior art been precipitated by hydrolysis with minute amounts of water entering with the feed, is removed with a filter 76 to avoid fouling of the heat exchange surface in the reactor loop.

The buildup of heavies in the system is controlled by directing a portion of the recycled second stage flash liquid to the ethylene absorber via 77, or, optionally, to the product fractionator. As indicated in FIG. 1 at 20, the flow of this stream can be controlled by a density controller or other analyzer means on the recirculating reactor loop stream.

It is desirable to kill the catalyst in the stream passing to the product fractionator 63 in order to prevent the production of undesirable heavies in that column. This can be done by the introduction of a small amount of water or stream into the feed to the product fractionator as depicted at 21 in FIG. 1. However, when the two-stage flash system is used as shown in FIG. 2 steam can be used in an ejecter 78 on the second stage flash vapor in order to also maintain the desired low pressure in the second stage flash vessel. Any suitable compression means can be substituted for the ejector.

The first flash zone 56 can be a heat exchanger located within the continuous closed path reaction zone as was discussed previously in respect to the embodiment shown in FIG. 1. When a heat exchanger is used, the reactor effluent is flashed into the shell side 79 of said heat exchanger.

The flashing of the reactor effluent in two stages allows recovery of nearly all the product as flashed vapor and thereby avoids the loss of active catalysts from the system. By reducing the catalyst loss from the reactor with reaction products, the catalyst usage would be decreased and productivity pushed even higher.

Figure 3:
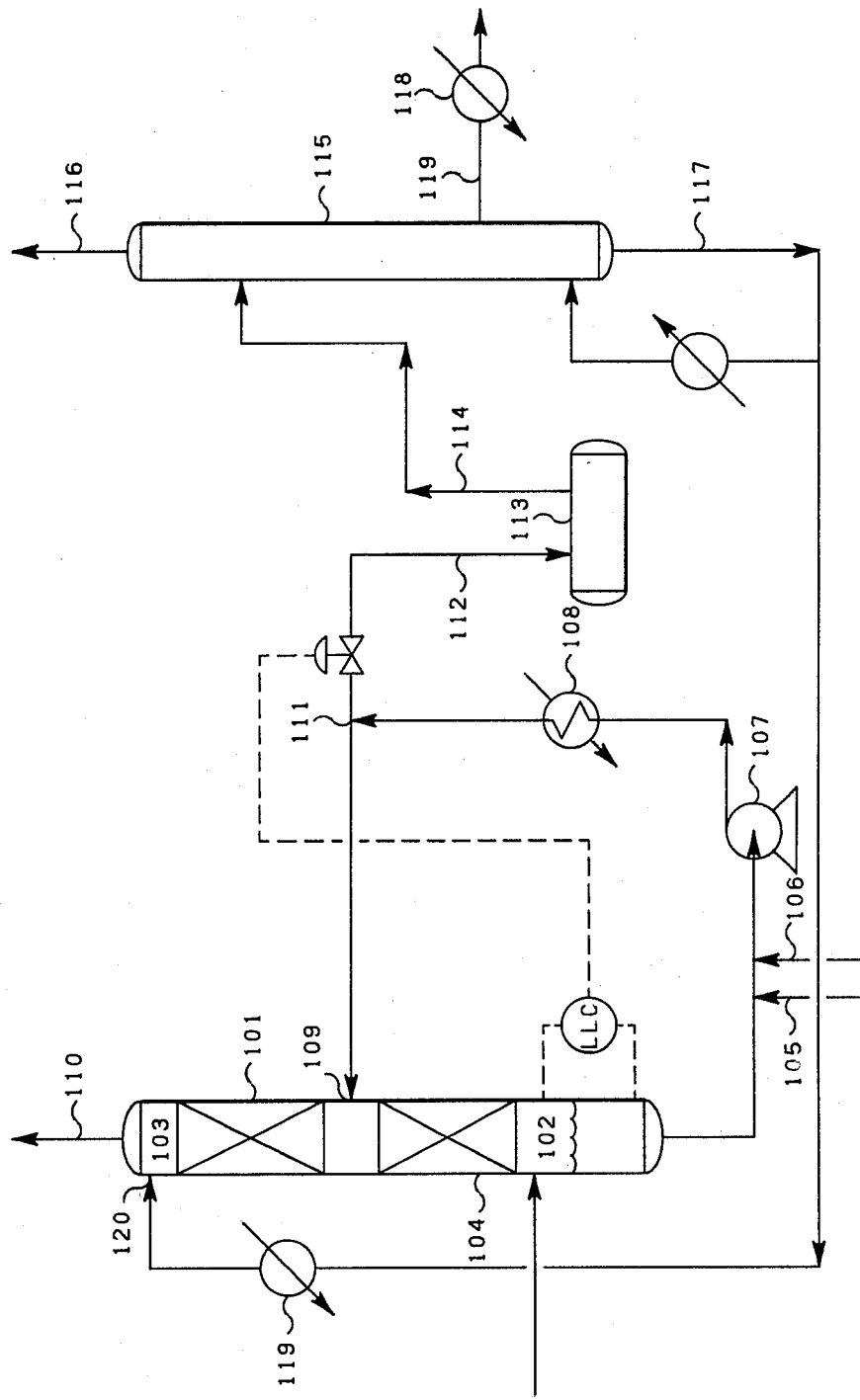
FIG. 3 shows the embodiment of the invention wherein a liquid-gas contactor is contained within the loop of the loop reactor. Product dimer is used as the absorbent for the unreacted ethylene within the contactor.

Referring to FIG. 3, an embodiment of the invention is depicted wherein a vapor liquid contacting tower is incorporated within the loop reactor. The vapor liquid contacting tower, e.g., a packed tower, is shown at 101. The vapor-liquid contacting tower shown in FIG. 3 comprises a lower section 102 which is used as a reacting zone with bottoms recycled to that zone and an upper section 103 which serves as an absorption zone.

Olefin feed, for example, an ethylene stream, enters the lower section of the tower 104. Catalyst used to initiate the dimerization reaction can be introduced into the system via 105 and 106 near the bottom of the absorber. Solvent or absorbent is introduced near the top of the tower at 120. The absorbent recovers unreacted ethylene with dimer product, product heavies or any suitable absorbent or solvent for ethylene that is known in the art as being an appropriate absorbent. The solvent has been recycled from product stripper 115 via conduit 117. The loop reactor is maintained at a temperature and pressure sufficient to liquefy butenes. The reaction stream in the continuous closed path reaction zone is continuously circulated by a pump 107. The reaction stream is also cooled by indirect heat exchanger 108 and returned to an intermediate point of the absorber at 109. Unreacted or unabsorbed gases such as hydrogen and methane are removed as absorber overhead at 110 and passed to storage or for further use as fuel gas.

A product side stream is continuously removed from the loop at 111 and passed via conduit means 112 to a catalyst removal zone 113. The product stream is then passed via 114 to product stripper 115 from which lights are vented overhead at 116, and product dimer is recovered at 121. The product dimer is cooled at 118 and passed to storage.

In another embodiment of the invention, a portion of the product dimer is passed via 117, cooled at 119 and introduced into the top of the absorber at 120. The recycled product dimer, therefore, functions as an absorbent to recover unreacted ethylene. In general, the solvent is recycled via 117, 119 and introduced at 120, whether it be dimer product, product heavies, or some other appropriate ethylene solvent. The absorbent recovers unreacted ethylene and keeps the ethylene from being lost overhead. The absorbent is removed in the product stripper at 117 and is continuously recycled to the top of the absorber tower. If the product dimer is used as absorbent, the dimerization of ethylene continually supplies additional dimer solvent to replace that being removed as product.

This embodiment has special application to low-concentration olefin streams, namely, gas streams with an olefin concentration of up to about 20 percent by volume. An example of such a stream is a dry gas vent stream from an ethylene cracking unit which can contain up to about 20 percent by volume ethylene, e.g., five percent of the product ethylene. The vent stream comprises such gases as hydrogen, methane, ethane, etc., and is usually used as field gas stream whereby the ethylene, unless separated, is lost. The use of ethylene purification facilities, however, would be very costly due to the low concentration of ethylene in the feed stream.

Figure 4:
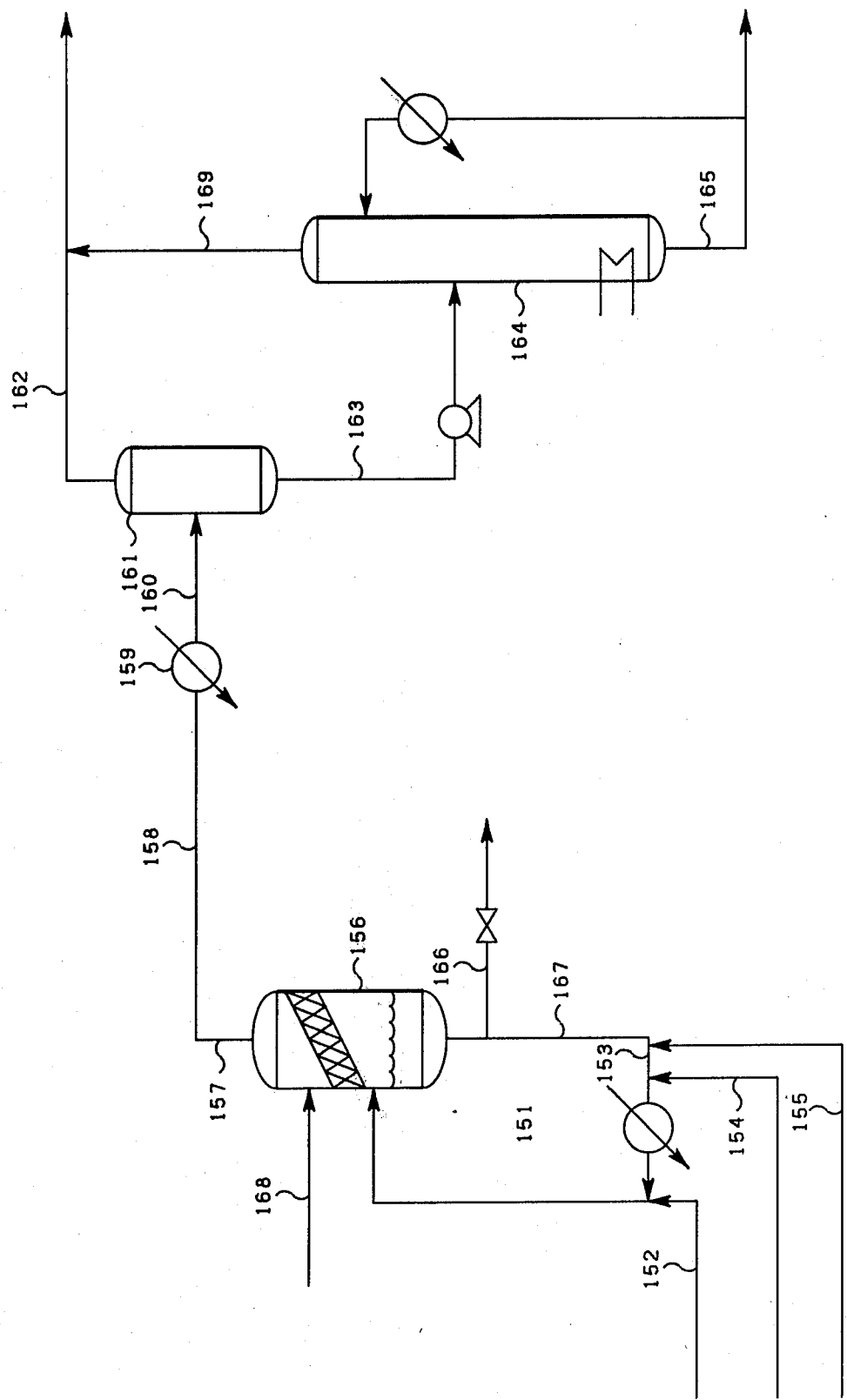
FIG. 4 is a schematic of the apparatus used in the olefin dimerization process wherein a thermosiphon-type loop reactor is utilized.

The use of the present invention, however, obviates the need for ethylene purification facilities other than for the removal of catalyst poisons such as water and sulfur compounds. The ethylene in the feed gas is dimerized to butenes which are much more easily recovered and separated from the gases than ethylene. As well, the recycled dimer keeps ethylene from being lost overhead to the field gas stream. The dimerization of ethylene to butene in order to recover it from fuel gas streams using a loop reactor containing an absorber or contacting tower within the loop is a much more efficient and economical process for the recovery of ethylene from a feed stream when the ethylene is present in a low concentration. FIG. 4 depicts another embodiment of the invention in which a thermosiphon-type loop reactor, such as the one disclosed in U.S. Pat. No. 3,213,157, is utilized to dimerize an olefin feed. A thermosiphon loop reactor is especially applicable to low-olefin-concentration feeds as the thermosiphon reactor minimizes the power requirements for the dimerization process in that it utilizes the energy of the feed gas to induce reactor circulation. A pump, therefore, is not needed to circulate the low concentration feed continuously through the loop reactor.

Referring now to FIG. 4, an olefin feed, which can be a low-concentration ethylene feed containing only about 20% by volume or less, e.g., approximately 5% ethylene, is introduced into loop reactor 151 via conduit 152. The energy of the feed gas is used to circulate the reactor liquid through the reactor. No pump is required in this continuous closed path reaction zone as previously depicted in FIGS. 1–3.

Catalyst, selective to dimerization, is introduced into the loop at 153 via conduits 154 and 155. The circulating liquid catalyst solvent should be a high boiling point material so that its vapor pressure would be very low at 100° F. (37.8° C.) in order to prevent excessive solvent loss to the gas stream. Additional make-up solvent can be added at 168.

The circulating reactor effluent passes through a separation zone 156 in which vapor is separated from liquid. Due to its vapor pressure and the large amount of "inert" gas, the product dimer butenes will remain with the gas stream until they are either chilled out or scrubbed out of the fuel gas stream. The product butenes and fuel gas stream are thereby removed overhead 157 and passed via conduit 158 to chiller 159. The overhead is then passed via 160 to a phase separation zone 161 from which fuel gas is recovered as overhead 162 and butene product is recovered as bottoms 163 which is then passed to recovery zone 164. Purified butene product is then recovered as bottoms 165 from said recovery zone.

A portion of the bottoms from separation zone 156 is removed at 166 in order to reprocess any spent catalyst. The remainder of the catalyst in bottoms liquid is recycled via 167 to the reactor.

In another embodiment of the invention (not shown in the drawing), an external absorbent, such as dimethylsulfoxide, is used to recover ethylene and heavies from the reactor effluent. The reactor effluent is contacted with the absorbent to remove the hydrocarbons and yield fuel gas as overhead. The hydrocarbons are then separated from the absorbent and charged to fractionation from which product dimer, e.g., butenes, is recovered and olefin, e.g., ethylene, is recycled to the dimerization reactor.

The process shown in FIG. 4 has the advantages that since the product butenes remain with the gas stream 158, no special catalyst removal or treatment of the product stream is required. Also, the use of the thermosiphon reactor minimizes energy requirements for circulating the material through the reactor since the energy from the feed gas is used to induce this circulation. The use of this gas lift-type reactor is especially economical energy-wise when using a low concentration ethylene feed due to the high concentration of inert gases.

The following examples demonstrate the invention with respect to the embodiments shown in FIGS. 1, 2, 3, and 4. The following embodiments are not intended to limit the invention in any way and are only given for illustration.

EXAMPLE I

The invention was demonstrated in a pilot plant loop reactor made up of 40 feet of one-inch OD stainless steel tubing with a total volume of about 2.6 gallons. Feed was high purity ethylene (99.9 wt. %) charged at 23.5 lbs/hr. Catalyst was a complex of nickel (II) chloride and tri-n-butylphosphine, namely, bis(tri-n-butylphosphine)dichloronickel. Reactor conditions were 92° F. (33° C.), 174 psia, and 33 minutes residence time.

Using the single flash reactor configuration of FIG. 1, ethylene conversion was 93.4 percent and catalyst productivity was 45,468 lbs. product per lb. nickel when flashed product was not recycled to the reactor loop. With recycle of flashed product as shown in FIG. 1, it has been calculated that catalyst productivity would increase to 389,600 pounds of product per pound of nickel. Compositions for the reactor effluent and the calculated flash at 90° F. (32° C.) and 30 psia are:

| | Stream Compositions, Mole Fraction | | |
|---|---|---|---|
| | Reactor Effluent | Flash Vapor | Flash Liquid |
| Stream No. | | (6) | (7) |
| Ethylene | 0.111 | 0.142 | 0.007 |
| Butene-1 | 0.040 | 0.045 | 0.026 |
| t-Butene-2 | 0.529 | 0.563 | 0.417 |
| c-Butene-2 | 0.228 | 0.239 | 0.191 |
| Heavies | 0.092 | 0.011 | 0.359 |
| Total | 1.000 | 1.000 | 1.000 |

EXAMPLE II

Calculations have been made to illustrate operation in the preferred mode of operation illustrated in FIG. 2. Reactor conditions are the same as for Example I, as are conditions for the first flash. Liquid from the first flash is further flashed at 90° F. (32° C.) and 5 psia to yield a heavies concentrate containing the catalyst which is recycled to the reactor.

| | Stream Compositions, Mole Fraction | | | |
|---|---|---|---|---|
| Stream No. | Reactor Effluent | First Flash Vapor (58) | First Flash Liquid (59) | Second Flash Vapor (62) | Second Flash Liquid (75) |
| Ethylene | 0.1000 | 0.1531 | 0.0070 | 0.0101 | 0.0001 |
| Butene-1 | 0.0386 | 0.0453 | 0.0267 | 0.0370 | 0.0040 |
| t-Butene-2 | 0.5042 | 0.5566 | 0.4123 | 0.5668 | 0.0746 |
| c-Butene-2 | 0.2169 | 0.2340 | 0.1871 | 0.2540 | 0.0410 |
| Heavies | 0.1403 | 0.0110 | 0.3669 | 0.1321 | 0.8803 |
| Totals | 1.0000 | 1.0000 | 1.0000 | 1.0000 | 1.0000 |

With this mode of operation, calculated catalyst productivity is about 9,000,000 pounds of product per pound of nickel.

EXAMPLE III

Calculations have been made to illustrate operation of the embodiment shown in FIG. 3. The illustrative process conditions are: a solvent to feed weight ratio of about 0.5, a reactor temperature of about 100° F. (38° C.), and reactor pressure of about 100 psia. The calculated material balance for the process shown in FIG. 3 is as follows:

| Stream No. | 104 lbs/day | wt. % | 105 lbs/day | 106 lbs/day | 110 lbs/day | wt. % |
|---|---|---|---|---|---|---|
| Hydrogen | 944,602 | 76.8 | | | 941,010 | 80.3 |
| Methane | 224,143 | 18.2 | | | 213,955 | 18.3 |
| Ethylene | 61,512 | 5.0 | | | 2,691 | 0.2 |
| Butenes | | | | | 14,609 | 1.2 |
| Solvent | | | | | | |
| Nickel Catalyst | | | | 10.0 | | |
| Aluminum Catalyst | | | 13.0 | | | |
| Total | 1,230,257 | 100.0 | 13.0 | 10.0 | 1,172,265 | 100.0 |

| | 112 lbs/day | 116 lbs/day | wt. % | 119 lbs/day | 117 lbs/day |
|---|---|---|---|---|---|
| Hydrogen | 3,592 | 3,592 | 22.0 | | |
| Methane | 10,188 | 10,188 | 62.3 | | |
| Ethylene | 385 | 385 | 2.4 | | |
| Butenes | 43,827 | 2,191 | 13.3 | 41,636 | |
| Solvent | 615,129 | | | | 615,129 |
| Nickel Catalyst | 10 | | | | |
| Aluminum Catalyst | 13 | | | | |
| Total | 673,144 | 16,356 | 100.0 | 41,636 | 615,129 |

EXAMPLE IV

The process shown in FIG. 4 is illustrated in the following calculated example. The reactor conditions of temperature and pressure are the same as in Example III.

| | MATERIAL BALANCE (LBS/DAY) | | | | | | | |
|---|---|---|---|---|---|---|---|---|
| Stream No. | 152 | 154 | 155 | 158 | 162 | 163 | 169 | 165 |
| Hydrogen | 944,602 | | | 944,602 | 944,580 | 22 | 22 | |
| Methane | 224,143 | | | 224,143 | 223,704 | 439 | 439 | |
| Ethylene | 61,512 | | | 3,076 | 2,699 | 377 | 377 | |
| Butenes | | | | 58,436 | 2.699 | 55,737 | 377 | 55,360 |
| Nickel Catalyst | | 1.0 | | | | | | |
| Aluminum Catalyst | | | 1.3 | | | | | |
| Total | 1,230,257 | 1.0 | 1.3 | 1,230,257 | 1,173,682 | 56,575 | 1,215 | 55,360 |

Reasonable variations and modifications which will become apparent to those skilled in the art can be made in the present invention without departing from the spirit and scope thereof.

I claim:

1. In a process for dimerizing an olefin which comprises:
   introducing said olefin into a continuous closed path reaction zone,
   reacting said olefin in the presence of a catalyst selective to dimerization and such conditions to result in the dimerization of the olefin,
   flashing the reaction mixture in a flashing zone to thereby form a flashed vapor and resultant liquid,
   recovering the product dimer from the flashed vapor of the flashing zone the improvement comprising carrying out said flashing in the shell side of a heat exchanger which is located in said continuous closed path reaction zone thereby removing part of the thermal heat of the dimerization.

2. A process in accordance with claim 1 further comprising the steps of:
   recycling a portion of the liquid flashed from the flashing zone to the reaction zone, and
   passing the remainder of the liquid obtained from the flashing zone to a recovery system for product recovery.

3. A process in accordance with claim 1 wherein the material flow in said continuous closed path reaction zone is maintained at a velocity in the range of about 6–20 ft/sec.

4. A process in accordance with claim 3 wherein said velocity is about 12 ft/sec.

5. A process in accordance with claim 1 wherein said olefin is ethylene.

6. A process in accordance with claim 1 wherein the product dimer is recovered from the flashed vapor in an absorption zone in which a portion of the product heavies is used as the absorbent.

7. A process in accordance with claim 1 wherein the liquid from the flashing zone is flashed in a second flashing zone, and
   the flashed vapor from said second flashing zone is passed to a fractionation zone for the recovery of product dimer.

8. A process in accordance with claim 7 wherein the flashed vapor from the first flashing zone is passed to an absorption zone,
   the bottoms from the absorption zone is passed to the fractionator zone,
   product dimer is recovered as overhead from the fractionation zone with bottoms from the fractionation zone passed to said absorption zone as absorbent, and
   a side stream comprised of olefin and absorbent is withdrawn from said absorption zone and is recycled to the reaction zone.

9. A process in accordance with claim 7 wherein the bottoms from said second flashing zone is filtered and recycled to the reaction zone.

10. In a process for dimerizing an olefin which comprises:
    introducing said olefin into a continuous closed path reaction zone,
    reacting said olefin in the presence of a catalyst selective to dimerization under such conditions as to result in the dimerization of the olefin, the improvement comprising arranging the lower section of a vapor liquid contacting zone in said continuous closed path,
    recovering unreacted olefin with a solvent introduced into the upper section of said liquid-vapor contacting zone,
    passing a portion of the bottom from said vapor-liquid contacting zone to a recovery system for the recovery of the dimer product and solvent with the remainder being recycled to the vapor-liquid contacting zone and being introduced just above said lower section of said vapor-liquid contacting zone, and
    recycling the solvent to the vapor-liquid contacting zone as absorbent for unreacted olefin.

11. A process in accordance with claim 10 wherein said olefin is introduced as a low concentration stream of gases and said solvent is product dimer thereby recovering one portion of the dimer as product and recycling a second portion to the vapor-liquid containing zone as absorbent for unreacted olefin.

12. A process in accordance with claim 10 wherein said olefin is ethylene and said catalyst is a mixture of a hydrocarbon-soluble nickel compound and an alkyl aluminum halide.

13. A process in accordance with claim 12 wherein the aluminum/nickel molar ratio in the catalyst components is in the range of about 2.1 to about 7.

14. A process in accordance with claim 10 wherein the material flow in the continuous closed path reaction zone is maintained at a velocity in the range of about 6–20 feet/sec.

15. A process for dimerizing an olefin which comprises introducing a feed gas containing said olefin into a continuous closed path reaction zone including a vertically extended reaction zone wherein the olefin is reacted in the presence of a catalyst selective to dimerization under such conditions to result in the dimerization of the olefin and the reaction mixture passes through the continuous closed path reaction zone solely by the energy imparted to said catalyst by the feed gas and density differential in the continuous closed path reaction zone.

16. A process in accordance with claim 15, wherein said olefin is in low concentration in said first gas.

17. A process in accordance with claim 16 wherein said olefin is ethylene.

* * * * *

UNITED STATES PATENT AND TRADEMARK OFFICE
CERTIFICATE OF CORRECTION

PATENT NO. : 4,242,531

DATED : December 30, 1980

INVENTOR(S) : Cecil O. Carter

It is certified that error appears in the above-identified patent and that said Letters Patent are hereby corrected as shown below:

Claim 11, column 12, line 30, delete "containing" and insert

--- contacting ---.

Signed and Sealed this

Eighth Day of September 1981

[SEAL]

Attest:

Attesting Officer

GERALD J. MOSSINGHOFF

Commissioner of Patents and Trademarks